US00PP33164P2

(12) United States Plant Patent
Johnson, Jr.

(10) Patent No.: US PP33,164 P2
(45) Date of Patent: Jun. 15, 2021

(54) ***BEGONIA* 'STERLING MOON'**

(50) Latin Name: ***Begonia* hybrid**
Varietal Denomination: Sterling Moon

(71) Applicant: Ozzie W. Johnson, Jr., Marietta, GA (US)

(72) Inventor: Ozzie W. Johnson, Jr., Marietta, GA (US)

( * ) Notice: Subject to any disclaimer, the term of this patent is extended or adjusted under 35 U.S.C. 154(b) by 0 days.

(21) Appl. No.: 17/028,271

(22) Filed: Sep. 22, 2020

(51) Int. Cl.
*A01H 6/18* (2018.01)
*A01H 5/02* (2018.01)

(52) U.S. Cl.
USPC ..... Plt./343

(58) Field of Classification Search
USPC ..... Plt./343
See application file for complete search history.

*Primary Examiner* — Annette H Para
(74) *Attorney, Agent, or Firm* — Cassandra Bright

(57) ABSTRACT

A new and distinct cultivar of *Begonia* plant named 'Sterling Moon' is disclosed, characterized by its distinctive silver mottled foliage, upright stems, improved root hardiness and large foliage. Flowers pink, flower buds are darker pink. The new cultivar is a *Begonia*, typically suited for garden and ornamental container use.

3 Drawing Sheets

Latin name of the genus and species: *Begonia* hybrid.
Variety denomination: 'Sterling Moon'.

BACKGROUND OF THE INVENTION

The new cultivar is a product of a planned breeding program. The new variety originated from a cross pollination of the seed parent, an unpatented, unnamed variety of *Begonia* hybrid with the pollen parent, a different *Begonia* hybrid, by the inventor during 2012. The crossing was made in Marietta, Ga. in the inventor's garden.

'Sterling Moon' was selected by the inventor, in 2013 Marietta, Ga. in the inventor's garden.

After selection of the new cultivar, asexual reproduction of 'Sterling Moon' was first performed in the same commercial greenhouse by leaf cuttings in 2014. 'Sterling Moon' has since produced several generations and has shown that the unique features of this cultivar are stable and reproduced true to type.

SUMMARY OF THE INVENTION

The cultivar 'Sterling Moon' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Sterling Moon.' These characteristics in combination distinguish 'Sterling Moon' as a new and distinct *Begonia* cultivar:

1. Distinctive silver mottled foliage.
2. Root hardiness.
3. Large leaf size.
4. Light pink flower and darker pink flower buds.
5. Large flower size.
6. Stems mainly upright.

PARENTAL COMPARISON

Plants of the new cultivar 'Sterling Moon' are similar to the female parent in most horticultural characteristics. However, plants of 'Sterling Moon' are larger and produce large foliage. Additionally, the new variety is more root hardy.

The pollen parent cannot be specifically identified.

COMMERCIAL COMPARISON

Plants of the new cultivar 'Sterling Moon' are similar to the commercial variety 'Metallic Mist' U.S. Plant Pat. No. 19,567 in most horticultural characteristics. However, 'Sterling Moon' differs in the following:

1. The new variety has more colorful foliage.
2. The new variety is more tolerant of heat and humidity.
3. The new variety is more root hardy.
4. The new variety has a larger leaf size
5. The new variety has a larger flower size
6. Plants of the new variety are larger.

Plants of the new cultivar 'Sterling Moon' are similar to the commercial variety 'Fireworks', unpatented, in most horticultural characteristics. However, 'Sterling Moon' differs in the following:

1. The new variety is more root hardy.
2. The new variety has a larger flower size
3. Plants of the new variety are larger and taller.

BRIEF DESCRIPTION OF THE PHOTOGRAPHS

The accompanying photograph in FIG. 1 illustrates in full color a typical plant of 'Sterling Moon' grown outdoors in Loxley, Ala. This plant is approximately 1 year old, planted in a 1 gallon pot.

Figure 1:
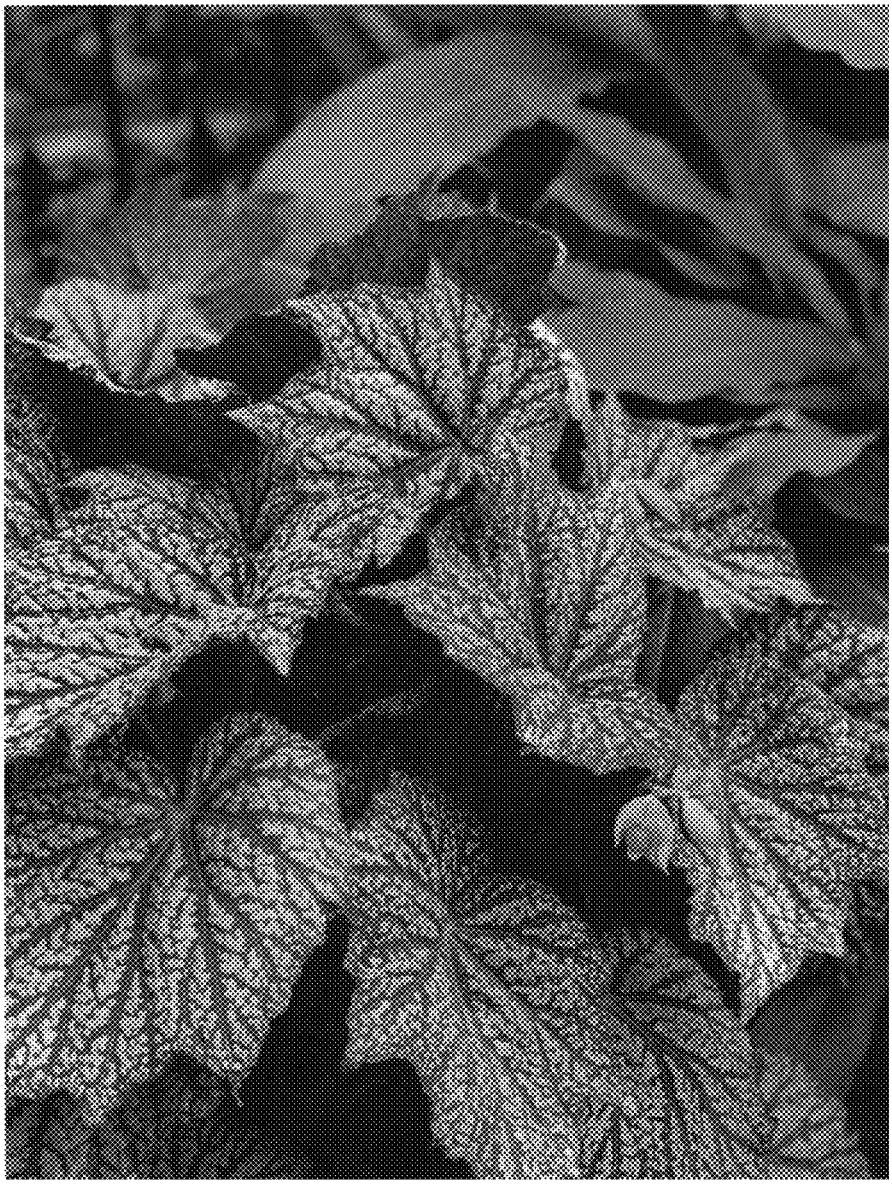
Figure 2:
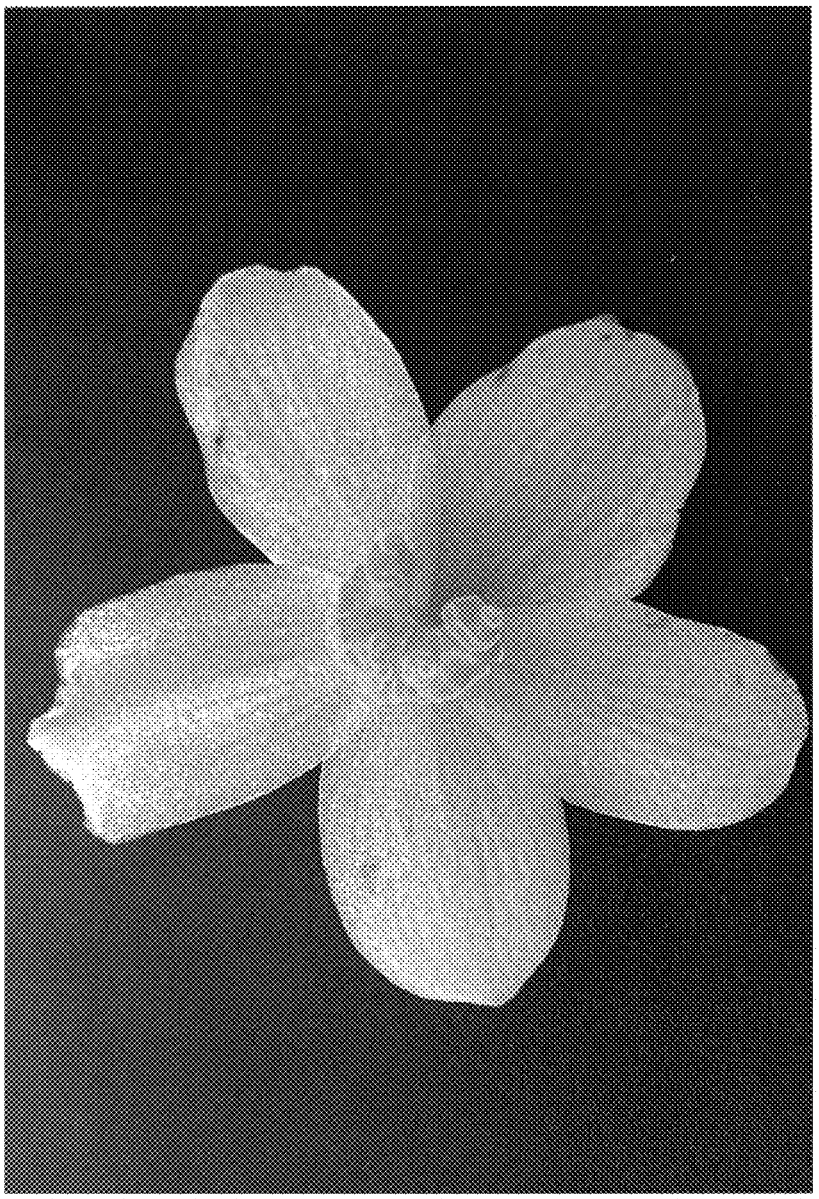
FIG. 2 illustrates a close-up of a mature flower.
Figure 3:
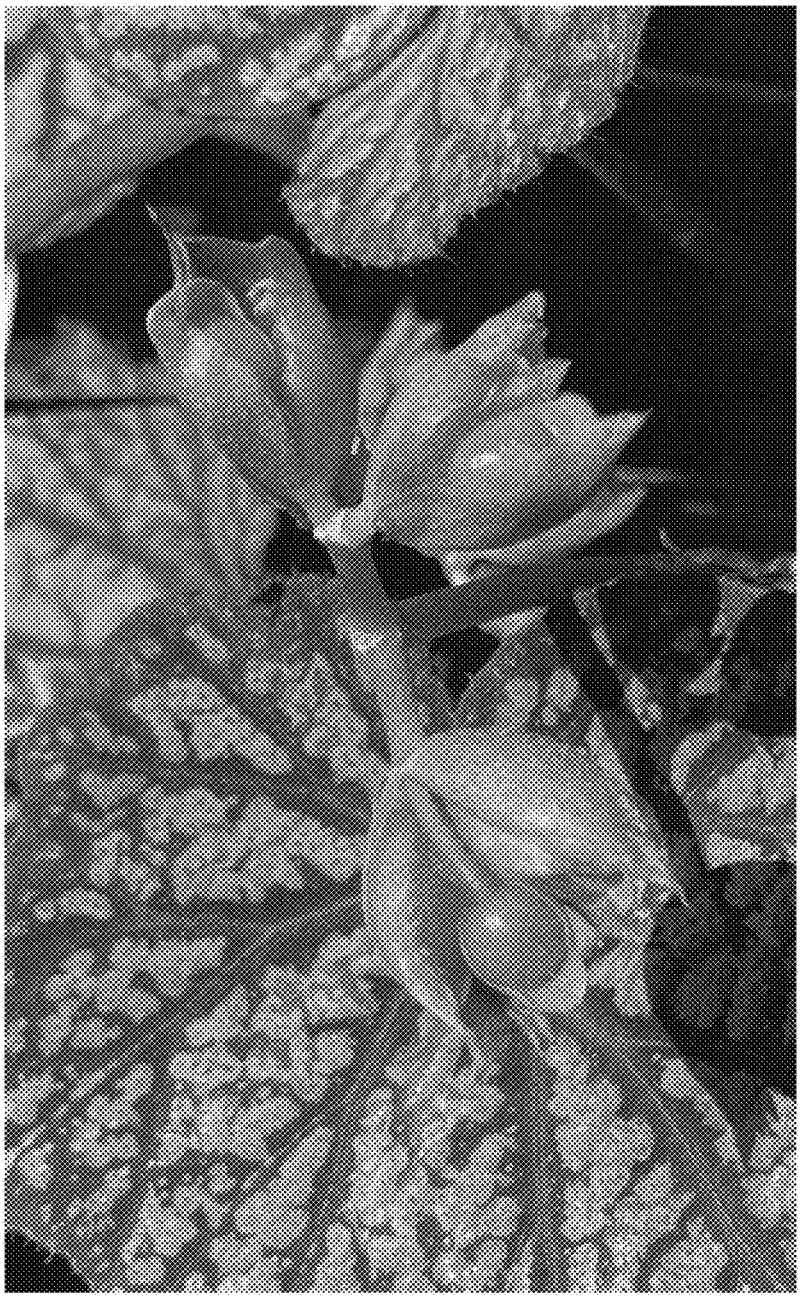
FIG. 3 illustrates a close-up view of flower buds.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Sterling Moon' plants grown in outdoors in Loxley, Ala. during Spring. Temperatures ranged from a low temperature about 55° F. at night to a high around 85° C. during the day. No artificial light, photoperiodic treatments or chemical treatments were given to the plants. Measurements and numerical values represent averages of typical plant types.

Botanical classification: *Begonia* hybrid 'Sterling Moon'.

Age of the plant described: Approximately 1 year.

Container size of the plant described: 2 gallon commercial container.

PROPAGATION

Typically reproduced commercially by tissue culture. Leaf cutting propagation is also possible.

PLANT

Growth habit: Upright flowering tender perennial.

Pot size of plant described: 2 gallon.

Height: Mature plants about 60 to 75 cm.

Plant spread: Mature plants about 45 to 60 cm.

Growth rate: Moderate to rapid.

Branching characteristics: Basal branching, breaking into 2 lateral branches at about 10 to 20 cm with maturity.

Quantity of branches: About 15 to 20.

Characteristics of branches:

*Length*.—About 15 cm.

*Form*.—Round in cross section.

*Diameter*.—Approximately 1.0 cm.

*Color*.—Near RHS Greyed-Purple 184C.

*Texture*.—Mainly glabrous. Very sparse, irregular hirsute hairs, about 4 mm long colored near White 155C.

*Strength*.—Weak to moderate.

Internode length: About 7 to 10 cm.

FOLIAGE

Arrangement: Emerging basally, with maturity 2 emerging from a branch split.

Quantity: Approximately 25 on a plant of this age.

Average length: Average range 15 to 17 cm.

Average width: Average range 12 to 14 cm.

Shape of blade: Broad kidney shaped.

Apex: Elongated acute.

Base: Cordate.

Margin: 5 Shallow lobes with very shallow crenation.

Texture of top surface: Glabrous, leathery.

Texture of bottom surface: Glabrous. Very sparse hirsute hairs along main veins.

Aspect: Puckered, overall flat.

Color:

*Young foliage upper side*.—Near RHS Greyed-Green 189C. Thick coloration along main veins near Greyed-Green N189A. Very slight overall flush near Greyed-Red 181D.

*Young foliage under side*.—Near RHS Greyed-Red 181B. Strong coloration along veins, Greyed-Purple 187C.

*Mature foliage upper side*.—Near RHS Greyed-Green 189C. Thick coloration along main veins near Greyed-Green N189A.

*Mature foliage under side*.—Near RHS Greyed-Red 181B. Strong coloration along veins, Greyed-Purple 187C.

Venation:

*Type*.—Palmate.

*Venation color upper side*.—Near RHS Greyed-Red 181D.

*Venation color under side*.—Near RHS Greyed-Purple 185A.

Petiole:

*Length*.—Average range 15 to 20 cm.

*Diameter*.—7 to 8 mm.

*Color*.—Near RHS Greyed-Red 181B.

*Texture*.—Glabrous. Rarely a hirsute hair bout 4 mm long.

Stipule description: 1 or 2 per node, non-fleshy, becoming completely dry and papery before leaves fully expand.

*Length*.—Approximately 3.0 cm.

*Diameter*.—Approximately 1.4 cm.

*Color*.—Begins near Greyed-Red 185A, turning Greyed-Orange 166D when dry.

*Texture*.—Glabrous.

FLOWER

Flowering habit: Continuously flowering during Spring and Summer. Flowering begins in May, in the Gulf Coast of the US.

Inflorescence and flower type and habit: Single flowers arranged in axillary cymes. Cymes held slightly above or within foliage, approximately 2 to 4 flowers per cyme.

Cyme size:

*Diameter*.—Approximately 9 cm.

*Height*.—Approximately 3.5 cm.

Flower longevity on plant: About 10 days, depending upon environmental conditions.

Persistent or self-cleaning: Self-Cleaning.

Bud:

*Shape*.—Ovate.

*Length*.—Approximately 2 cm, including bracts. Tepal bud alone about 1.3 cm.

*Diameter*.—Approximately 1 cm, including bracts. Tepal bud alone about 1.0 cm.

*Color*.—Tepal bud near RHS Red 52B. Immature bracts around bud colored near Red 49B.

Flower size:

*Diameter*.—Approximately 4.0 cm.

*Depth*.—Approximately 2.5 cm, including protruding stamens.

Tepals:

*Quantity*.—Approximately 5.

*Arrangement*.—Rotate.

*Length*.—Approximately 2.2 cm.

*Width*.—Approximately 1.3 cm.

*Shape*.—Ovate.

*Apex*.—Obtuse.

*Base*.—Broad attenuate.

*Margin*.—Entire.

*Aspect*.—Slight upward curve.

*Texture, upper and lower surfaces*.—Matte.

*Appearance, upper and lower surfaces*.—Slightly iridescent.

Color:
*When opening, upper surface*.—Near RHS Red 55C.
*When opening, lower surface*.—Near RHS Red 55C streaked 55A.
*Fully opened, upper surface*.—Near RHS Red 56D streaked 55D.
*Fully opened, lower surface*.—Near RHS Red 56D streaked 55B.
Flower bracts:
*Quantity per flower*.—2.
*Shape*.—Ovate, strongly concave.
*Length*.—Approximately 3.0 cm.
*Diameter*.—Approximately 1.8 cm, when manually flattened.
*Apex*.—Acute.
*Base*.—Truncate.
*Margin*.—Entire.
*Texture*.—Glabrous.
*Aspect*.—Strongly curved inward towards tepals.
*Color*.—Near RHS Red 51C when mature. Immature bracts near Red 49B.
Peduncles:
*Length*.—Average 16 cm.
*Diameter*.—Approximately 4 mm.
*Angle*.—About 15° to the lateral branch.
*Strength*.—Moderate, flexible.
*Texture*.—Glabrous.
*Color*.—Near RHS Greyed-Red 181C.
Pedicels:
*Length*.—Approximately 2.5 cm.
*Diameter*.—Approximately 3 mm.
*Angle*.—About 45° to the lateral branch.
*Strength*.—Moderate, flexible.
*Texture*.—Glabrous.
*Color*.—Near RHS Yellow-Green 145D lightly flushed Red 49D.
Fragrance: None.

REPRODUCTIVE ORGANS

Stamens:
*Number*.—8, arising from staminoidal column.
Anthers:
*Description*.—Fleshy, curly.
*Length*.—Free portion about 7 mm.
*Color*.—Near RHS Green-Yellow 1A.
*Pollen*.—Scant to none. Colored near Yellow 4D.
Pistil:
*Number*.—1.
*Length*.—Approximately 1.8 cm.
*Style*.—Length: Approximately 2 mm. Color: Near RHS Yellow-Green 145B.
*Stigma*.—Shape: Linear. Color: Near RHS Yellow-Green 145D. Ovary Color: Near RHS Yellow-Green 145B.

OTHER CHARACTERISTICS

Seeds: Not observed.
Disease/pest resistance: Moderate resistance and susceptibility to common diseases and pests of *Begonia* have been observed in the new variety.
Temperature tolerance: USDA Zone 7-9.

What is claimed is:

1. A new and distinct cultivar of *Begonia* plant named 'Sterling Moon' as herein illustrated and described.

* * * * *